US009408870B2

(12) United States Patent
Saji et al.

(10) Patent No.: US 9,408,870 B2
(45) Date of Patent: Aug. 9, 2016

(54) ORAL CARE COMPOSITION

(75) Inventors: Maya Treesa Saji, Bangalore (IN);
Ritesh Kumar Sinha, Bangalore (IN)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 13/990,480

(22) PCT Filed: Nov. 17, 2011

(86) PCT No.: PCT/EP2011/070317
§ 371 (c)(1),
(2), (4) Date: Jul. 10, 2013

(87) PCT Pub. No.: WO2012/076310
PCT Pub. Date: Jun. 14, 2012

(65) Prior Publication Data
US 2013/0295027 A1  Nov. 7, 2013

(30) Foreign Application Priority Data

Dec. 7, 2010  (IN) .................... 3322/MUM/2010
Jan. 25, 2011  (EP) ....................... 11151950

(51) Int. Cl.
| A61K 33/42 | (2006.01) |
| A61K 31/05 | (2006.01) |
| A61K 31/315 | (2006.01) |
| A61K 33/30 | (2006.01) |
| A61K 8/27 | (2006.01) |
| A61K 8/34 | (2006.01) |
| A61Q 11/00 | (2006.01) |
| A61K 8/92 | (2006.01) |

(52) U.S. Cl.
CPC . *A61K 33/42* (2013.01); *A61K 8/27* (2013.01); *A61K 8/34* (2013.01); *A61K 8/347* (2013.01); *A61K 8/922* (2013.01); *A61K 31/05* (2013.01); *A61K 31/315* (2013.01); *A61K 33/30* (2013.01); *A61Q 11/00* (2013.01)

(58) Field of Classification Search
None
See application file for complete search history.

(56) References Cited

U.S. PATENT DOCUMENTS

| 658,596 | A | 9/1900 | Simpson |
| 2,196,763 | A | 4/1940 | Figg, Jr. |
| 2,359,241 | A | 9/1944 | Partansky |
| 3,120,469 | A | 2/1964 | Tamas |
| 3,256,310 | A | 6/1966 | Weil |
| 3,779,932 | A | 12/1973 | Jaggers et al. |
| 3,787,566 | A | 1/1974 | Gauvreau |
| 3,966,627 | A | 6/1976 | Gray |
| 4,267,168 | A | 5/1981 | Van Leuven |
| 4,284,434 | A | 8/1981 | Lingmann et al. |
| 4,474,798 | A | 10/1984 | Inagi et al. |
| 4,548,809 | A | 10/1985 | Fung |
| 4,597,887 | A | 7/1986 | Colodney et al. |
| 4,966,754 | A | 10/1990 | Purohit |
| 4,992,259 | A | 2/1991 | Schiraldi et al. |
| 5,013,486 | A | 5/1991 | Joshi |
| 5,073,366 | A | 12/1991 | Beck |
| 5,283,056 | A | 2/1994 | Chung et al. |
| 5,322,638 | A | 6/1994 | Schadt et al. |
| 5,328,682 | A | 7/1994 | Pullen et al. |
| 5,435,935 | A | 7/1995 | Kupneski |
| 5,472,684 | A * | 12/1995 | Nabi et al. .............. 424/49 |
| 5,474,712 | A | 12/1995 | Dotolo |
| 5,474,761 | A | 12/1995 | Liang |
| 5,591,708 | A | 1/1997 | Richter |
| 5,610,189 | A | 3/1997 | Whiteley |
| 5,763,468 | A | 6/1998 | Barranx et al. |
| 5,817,295 | A | 10/1998 | Chaudhari et al. |
| 5,939,050 | A | 8/1999 | Iyer |
| 5,942,478 | A | 8/1999 | Lopes |
| 5,965,518 | A | 10/1999 | Nakatsu et al. |
| 6,048,368 | A | 4/2000 | Tcheou et al. |
| 6,048,836 | A | 4/2000 | Romano et al. |
| 6,066,674 | A | 5/2000 | Hioki |
| 6,103,683 | A | 8/2000 | Romano et al. |
| 6,110,883 | A | 8/2000 | Petri et al. |
| 6,114,298 | A | 9/2000 | Petri |
| 6,121,315 | A * | 9/2000 | Nair et al. .............. 514/494 |
| 6,177,388 | B1 | 1/2001 | Cheung et al. |

(Continued)

FOREIGN PATENT DOCUMENTS

| CH | 692411 | 6/2002 |
| CN | 1071998 | 10/2001 |

(Continued)

OTHER PUBLICATIONS

Mintel, Antibacterial Fluride Toothpaste, Antibacterial Fluride Toothpaste, Nov. 2007, NA, NA, NZ.

(Continued)

*Primary Examiner* — Frederick Krass
*Assistant Examiner* — Michael P Cohen
(74) *Attorney, Agent, or Firm* — Ronald A. Koatz

(57) ABSTRACT

The present invention relates to an oral care composition and a method of disinfecting the oral cavity. So far synthetic material (e.g. Triclosan) has been used which is believed by many consumers to be harsh on them. Consumers, more and more prefer using products that contain natural materials. Further, in many countries, culturally or otherwise, people are reluctant to using alcohol in their mouthwashes. The present inventors have been working on solving these problems and have come up with an oral care composition which includes natural materials that are found to interact synergistically with certain metal salts in killing *S. mutans*, a bacterium responsible for tooth decay.

11 Claims, No Drawings

(56) References Cited

U.S. PATENT DOCUMENTS

| | | |
|---|---|---|
| 6,183,766 B1 | 2/2001 | Sine et al. |
| 6,190,674 B1 | 2/2001 | Beerse et al. |
| 6,210,695 B1 | 4/2001 | Beerse et al. |
| 6,248,705 B1 | 6/2001 | Cardola et al. |
| 6,261,540 B1 | 7/2001 | Nelson |
| 6,277,805 B1 | 8/2001 | Kupneski |
| 6,323,166 B1 | 11/2001 | Kamiya |
| 6,455,086 B1 | 9/2002 | Trinh et al. |
| 6,458,753 B1 | 10/2002 | Haylett |
| 6,506,707 B1 | 1/2003 | Bessette |
| 6,521,578 B1 | 2/2003 | Stute et al. |
| 6,531,115 B1 | 3/2003 | Singh |
| 6,534,042 B2 | 3/2003 | Delli Santi et al. |
| 6,537,955 B1 | 3/2003 | Raso et al. |
| 6,576,247 B1 | 6/2003 | Ikemoto et al. |
| 6,607,733 B1 | 8/2003 | Diec |
| 6,613,728 B1 | 9/2003 | Sirianni et al. |
| 6,624,126 B1 | 9/2003 | Kasuga et al. |
| 6,645,472 B1 | 11/2003 | Anderson |
| 6,730,643 B2 | 5/2004 | Chokappa et al. |
| 6,753,305 B2 | 6/2004 | Raso et al. |
| 6,841,090 B1 | 1/2005 | Serego Allighieri et al. |
| 6,861,402 B1 | 3/2005 | Miracle |
| 6,902,726 B1 | 6/2005 | Varel |
| 6,921,745 B2 | 7/2005 | Yamada et al. |
| 7,754,774 B2 | 7/2010 | Kobayashi et al. |
| 8,066,979 B1 | 11/2011 | Dickens |
| 2001/0000029 A1 | 3/2001 | Misumi |
| 2002/0002124 A1 | 1/2002 | Biedermann et al. |
| 2002/0081270 A1 | 6/2002 | Delli Santi |
| 2002/0107287 A1 | 8/2002 | Bessette et al. |
| 2002/0176879 A1 | 11/2002 | Dodd et al. |
| 2002/0182268 A1 | 12/2002 | Bessette et al. |
| 2003/0044441 A1 | 3/2003 | Schmid et al. |
| 2003/0044469 A1 | 3/2003 | Viladot Petit et al. |
| 2003/0077233 A1 | 4/2003 | Suckerman |
| 2003/0083212 A1 | 5/2003 | Willard et al. |
| 2003/0096722 A1 | 5/2003 | Caselli et al. |
| 2003/0129150 A1 | 7/2003 | Pauly et al. |
| 2003/0138394 A1 | 7/2003 | Charrouf et al. |
| 2003/0138502 A1 | 7/2003 | Pauly et al. |
| 2003/0147963 A1 | 8/2003 | De Moragas et al. |
| 2003/0152536 A1 | 8/2003 | Pauly et al. |
| 2003/0231978 A1 | 12/2003 | Franklin et al. |
| 2004/0014818 A1 | 1/2004 | Boeck et al. |
| 2004/0028697 A1 | 2/2004 | Pauly et al. |
| 2004/0042996 A1 | 3/2004 | Pauly et al. |
| 2004/0044078 A1 | 3/2004 | Kawa et al. |
| 2004/0047832 A1 | 3/2004 | Pauly et al. |
| 2004/0063601 A1 | 4/2004 | Denome et al. |
| 2004/0067203 A1 | 4/2004 | Parikh |
| 2004/0081714 A1 | 4/2004 | Pauly et al. |
| 2004/0096479 A1 | 5/2004 | Levine |
| 2004/0105836 A1 | 6/2004 | Seipel et al. |
| 2004/0115158 A1 | 6/2004 | Schieferstein et al. |
| 2004/0142007 A1 | 7/2004 | Moussou et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0198630 A1 | 10/2004 | Schmid et al. |
| 2004/0209795 A1 | 10/2004 | Vlad |
| 2004/0234480 A1 | 11/2004 | Pauly et al. |
| 2005/0019431 A1 | 1/2005 | Modak et al. |
| 2005/0065055 A1 | 3/2005 | Barnes |
| 2005/0077497 A1 | 4/2005 | Anderson |
| 2005/0089497 A1 | 4/2005 | Prinz et al. |
| 2005/0089499 A1 | 4/2005 | Moussou et al. |
| 2005/0119153 A1 | 6/2005 | Burt et al. |
| 2005/0143277 A1 | 6/2005 | Dufay et al. |
| 2005/0172859 A1 | 8/2005 | Nieendick et al. |
| 2005/0184275 A1 | 8/2005 | Mora-Gutierrez et al. |
| 2005/0233930 A1 | 10/2005 | Cheung et al. |
| 2005/0256021 A1 | 11/2005 | Lu |
| 2006/0008482 A1 | 1/2006 | Prinz et al. |
| 2006/0039956 A1 | 2/2006 | Hensen et al. |
| 2006/0040847 A1 | 2/2006 | Weibel |
| 2006/0045914 A1 | 3/2006 | Narayanan |
| 2006/0057090 A1 | 3/2006 | Buchwald-Werner |
| 2006/0079414 A1 | 4/2006 | Nieendick et al. |
| 2006/0093570 A1 | 5/2006 | Duddington et al. |
| 2006/0128585 A1 | 6/2006 | Adair et al. |
| 2006/0134013 A1 | 6/2006 | Sharma |
| 2006/0141073 A1 | 6/2006 | Worrell |
| 2006/0153959 A1 | 7/2006 | Behan et al. |
| 2006/0165631 A1 | 7/2006 | Danoux et al. |
| 2006/0165820 A1 | 7/2006 | Yatcilla |
| 2006/0270571 A1 | 11/2006 | Burke et al. |
| 2006/0276336 A1 | 12/2006 | Sardo |
| 2007/0014878 A1 | 1/2007 | Gardiner |
| 2007/0053849 A1 | 3/2007 | Doyle et al. |
| 2007/0081966 A1 | 4/2007 | Behler et al. |
| 2007/0104676 A1 | 5/2007 | Moser et al. |
| 2007/0154414 A1 | 7/2007 | Bonfiglio |
| 2007/0218016 A1 | 9/2007 | Rabenhorst et al. |
| 2007/0227930 A1 | 10/2007 | Bromberg et al. |
| 2007/0231295 A1 | 10/2007 | Hoppe |
| 2007/0237847 A1 | 10/2007 | Henry et al. |
| 2007/0258991 A1 | 11/2007 | Buasen et al. |
| 2007/0258996 A1 | 11/2007 | Mookerjee et al. |
| 2007/0270321 A1 | 11/2007 | Barnhart et al. |
| 2008/0008660 A1 | 1/2008 | Rabenhorst et al. |
| 2008/0026974 A1 | 1/2008 | Barnhart et al. |
| 2008/0032908 A1 | 2/2008 | Kurtz |
| 2008/0044479 A1 | 2/2008 | Stack |
| 2008/0045491 A1 | 2/2008 | Fitchmun |
| 2008/0051312 A1 | 2/2008 | Lestage et al. |
| 2008/0064711 A1 | 3/2008 | Friedman |
| 2008/0096790 A1 | 4/2008 | Behan et al. |
| 2008/0107742 A1 | 5/2008 | Hare |
| 2008/0118591 A1 | 5/2008 | Natsch |
| 2008/0160000 A1 | 7/2008 | Motozono et al. |
| 2008/0171709 A1 | 7/2008 | Remmal |
| 2008/0194675 A1 | 8/2008 | Bettuzzi |
| 2008/0207480 A1 | 8/2008 | Pipko |
| 2008/0214432 A1 | 9/2008 | Gaudin |
| 2008/0214518 A1 | 9/2008 | Remmal |
| 2008/0214568 A1 | 9/2008 | Remmal |
| 2008/0220036 A1 | 9/2008 | Miltz et al. |
| 2008/0221003 A1 | 9/2008 | Meine et al. |
| 2008/0253976 A1 | 10/2008 | Scott |
| 2008/0255247 A1 | 10/2008 | Sagalowicz et al. |
| 2008/0274072 A1 | 11/2008 | Manolas et al. |
| 2008/0299200 A1 | 12/2008 | Leser et al. |
| 2008/0299220 A1 | 12/2008 | Tamarkin et al. |
| 2009/0004308 A1 | 1/2009 | Frehner et al. |
| 2009/0035228 A1 | 2/2009 | Modak |
| 2009/0105195 A1 | 4/2009 | O'Brien |
| 2009/0165228 A1 | 7/2009 | Kilkenny et al. |
| 2009/0176887 A1 | 7/2009 | Vlasaty et al. |
| 2009/0264329 A1 | 10/2009 | Underwood et al. |
| 2009/0317431 A1 | 12/2009 | Schaefer |
| 2010/0003198 A1 | 1/2010 | Stolmeier et al. |
| 2010/0047294 A1 | 2/2010 | Ahlnas |
| 2010/0061946 A1 | 3/2010 | Scherner et al. |
| 2010/0129302 A1 | 5/2010 | Ahlnas |
| 2010/0172875 A1 | 7/2010 | Phan et al. |
| 2010/0183539 A1 | 7/2010 | Bernhardt et al. |
| 2010/0184855 A1 | 7/2010 | Bernhardt et al. |
| 2011/0223114 A1 | 9/2011 | Chakrabortty et al. |
| 2012/0003163 A1 | 1/2012 | Mordas |
| 2012/0004641 A1 | 1/2012 | Bruehwiler et al. |
| 2014/0170198 A1 | 6/2014 | Franklin et al. |

FOREIGN PATENT DOCUMENTS

| | | |
|---|---|---|
| CN | 1669576 | 9/2005 |
| CN | 101036459 | 9/2007 |
| CN | 101076315 | 11/2007 |
| CN | 101313772 | 12/2008 |
| CN | 101590287 | 12/2009 |
| CN | 101601382 | 12/2009 |
| CN | 101874531 | 11/2010 |
| CN | 102229861 | 11/2011 |
| CN | 101601382 | 8/2012 |

(56) References Cited

FOREIGN PATENT DOCUMENTS

| | | |
|---|---|---|
| DE | 2263126 | 7/1973 |
| DE | 2263136 | 7/1973 |
| DE | 2445676 | 4/1976 |
| DE | 3117792 | 11/1982 |
| DE | 19509079 | 9/1996 |
| DE | 102004038285 | 4/2006 |
| EA | EP1561476 | 8/2005 |
| EP | 0112141 | 12/1983 |
| EP | 0129987 | 11/1986 |
| EP | 621335 | 10/1994 |
| EP | 715856 | 6/1996 |
| EP | 0916718 | 10/1997 |
| EP | 0916720 | 5/1999 |
| EP | 0948892 | 10/1999 |
| EP | 950399 | 10/1999 |
| EP | 0966883 | 12/1999 |
| EP | 0995425 | 4/2000 |
| EP | 1146111 | 4/2000 |
| EP | 1013261 | 6/2000 |
| EP | 1170006 | 1/2002 |
| EP | 1079703 B | 8/2002 |
| EP | 0912098 | 4/2003 |
| EP | 1604643 | 12/2005 |
| EP | 1607098 | 12/2005 |
| EP | 1661976 | 5/2006 |
| EP | 1672054 | 6/2006 |
| EP | 1194461 | 10/2008 |
| EP | 2018869 | 1/2009 |
| EP | 2047889 | 4/2009 |
| EP | 2348838 | 5/2013 |
| ES | 2074030 | 8/1995 |
| FR | 861920 | 2/1941 |
| FR | 1137 M | 5/1961 |
| FR | 1137 M | 2/1962 |
| FR | 861920 | 2/1962 |
| FR | 1356209 | 3/1964 |
| FR | 2697133 | 4/1994 |
| FR | 2752730 | 3/1998 |
| GB | 366870 | 2/1932 |
| GB | 508407 | 6/1939 |
| GB | 1395839 | 5/1975 |
| GB | 1420946 | 1/1976 |
| GB | 2307915 | 6/1997 |
| GB | 2319181 | 5/1998 |
| GB | 2320927 | 7/1998 |
| GB | 2322552 | 9/1998 |
| GB | 2341092 | 3/2000 |
| GB | 2393911 | 4/2004 |
| JP | 2196718 | 3/1990 |
| JP | 03-011013 | 1/1991 |
| JP | 8151324 | 6/1996 |
| JP | 9241139 | 9/1997 |
| JP | H10114636 | 5/1998 |
| JP | 11130642 | 5/1999 |
| JP | 11228368 | 8/1999 |
| JP | 11315012 | 11/1999 |
| JP | 2000026260 | 1/2000 |
| JP | 2000063262 | 2/2000 |
| JP | 2000344641 | 12/2000 |
| JP | 2001342500 | 12/2001 |
| JP | 2003113013 | 4/2003 |
| JP | 2004075798 | 3/2004 |
| JP | 2004123674 | 4/2004 |
| JP | 2004203839 | 7/2004 |
| JP | JP2005015368 | 1/2005 |
| JP | 2005065750 | 3/2005 |
| JP | 2005239965 | 9/2005 |
| JP | 2005298357 | 10/2005 |
| JP | 200695182 | 4/2006 |
| JP | 2006307231 | 11/2006 |
| JP | 2009196987 | 9/2009 |
| JP | 2010037272 | 2/2010 |
| JP | 2012250937 | 12/2012 |
| KR | 020030181 | 4/2002 |
| KR | 20020030181 | 4/2002 |
| KR | 20020032949 | 5/2002 |
| KR | 20030070487 | 8/2003 |
| KR | 100885511 | 2/2009 |
| KR | 20100123424 | 11/2010 |
| KR | 20120093607 | 8/2012 |
| RU | 2228168 | 5/2004 |
| RU | 2263115 | 10/2005 |
| RU | 2277923 | 6/2006 |
| RU | 2277923 C2 | 6/2006 |
| SE | CH692411 | 6/2002 |
| SU | 1644963 | 4/1991 |
| WO | WO9218091 | 10/1992 |
| WO | WO9512379 | 5/1995 |
| WO | WO9611694 | 4/1996 |
| WO | WO9623050 | 8/1996 |
| WO | WO9715277 | 5/1997 |
| WO | WO9725106 | 7/1997 |
| WO | WO9726855 | 7/1997 |
| WO | WO9730586 | 8/1997 |
| WO | WO9731092 | 8/1997 |
| WO | WO9731093 | 8/1997 |
| WO | WO9801524 | 1/1998 |
| WO | WO9802044 | 1/1998 |
| WO | WO9802139 | 1/1998 |
| WO | WO9811867 | 3/1998 |
| WO | WO9824314 | 6/1998 |
| WO | WO9844959 | 10/1998 |
| WO | WO9854279 | 12/1998 |
| WO | WO9855080 | 12/1998 |
| WO | WO9855092 | 12/1998 |
| WO | WO9855093 | 12/1998 |
| WO | WO9855094 | 12/1998 |
| WO | WO9855095 | 12/1998 |
| WO | WO9936033 | 7/1999 |
| WO | WO9952360 | 10/1999 |
| WO | WO9958631 | 11/1999 |
| WO | WO00166 | 1/2000 |
| WO | WO0025763 | 5/2000 |
| WO | WO0027981 | 5/2000 |
| WO | WO0051436 | 9/2000 |
| WO | WO0061106 | 10/2000 |
| WO | WO0118201 | 3/2001 |
| WO | WO0121753 | 3/2001 |
| WO | WO0167868 | 9/2001 |
| WO | WO0170215 | 9/2001 |
| WO | WO0179409 | 10/2001 |
| WO | WO02065859 | 8/2002 |
| WO | WO02096435 | 12/2002 |
| WO | WO03034994 | 5/2003 |
| WO | WO03037270 | 5/2003 |
| WO | WO03050224 | 6/2003 |
| WO | WO03091375 | 11/2003 |
| WO | WO03095600 | 11/2003 |
| WO | WO2004006679 | 1/2004 |
| WO | WO2004032886 | 4/2004 |
| WO | WO2004035723 | 4/2004 |
| WO | WO2005094385 | 10/2005 |
| WO | WO03010273 | 2/2006 |
| WO | WO2006012715 | 2/2006 |
| WO | WO2006042661 | 4/2006 |
| WO | WO2006053458 | 5/2006 |
| WO | WO2006109898 | 10/2006 |
| WO | WO2007063268 | 6/2007 |
| WO | WO2007065538 | 6/2007 |
| WO | WO2007110790 | 10/2007 |
| WO | WO2007125216 | 11/2007 |
| WO | WO2008017484 | 2/2008 |
| WO | WO2008028278 | 3/2008 |
| WO | WO2008034549 | 3/2008 |
| WO | WO2008035101 | 3/2008 |
| WO | WO2008060130 | 5/2008 |
| WO | WO2008061658 | 5/2008 |
| WO | WO2008085446 | 7/2008 |
| WO | WO2008088827 | 7/2008 |
| WO | WO2008125884 | 10/2008 |
| WO | WO2008157847 | 12/2008 |
| WO | WO2009000097 | 12/2008 |
| WO | WO2009023731 | 2/2009 |
| WO | WO2009026949 | 3/2009 |

(56) References Cited

FOREIGN PATENT DOCUMENTS

| | | |
|---|---|---|
| WO | WO2009083521 | 7/2009 |
| WO | WO2009085058 | 7/2009 |
| WO | WO2009090648 | 7/2009 |
| WO | WO2009113910 | 9/2009 |
| WO | WO2009128012 | 10/2009 |
| WO | WO2010046238 A1 | 4/2010 |
| WO | WO 2010046238 A1 * | 4/2010 |
| WO | WO2011023582 | 3/2011 |
| WO | WO2011036048 | 3/2011 |
| WO | WO2011039630 | 4/2011 |
| WO | WO2011151169 | 12/2011 |
| WO | WO2011151171 | 12/2011 |
| WO | WO2011151172 | 12/2011 |
| WO | WO2012018519 | 2/2012 |
| WO | WO2013083581 | 6/2013 |
| WO | WO2013083586 | 6/2013 |
| WO | WO2013083587 | 6/2013 |
| WO | WO2013083588 | 6/2013 |

OTHER PUBLICATIONS

Mintel, Mouth Rinse, Mouth Rinse, Oct. 2007, NA, NA, GB.
PCT International Search Report in PCT application PCT/EP2011/070317 dated Jan. 26, 2012 with Written Opinion.
European Search Report in EP application EP 11 15 1950 dated Jun. 24, 2011.
PCT International Search Report in PCT application PCT/EP2011/070093 dated Feb. 6, 2012 with Written Opinion.
Co-pending Application: Applicant: Rout et al., U.S. Appl. No. 13/990,475, filed Jul. 10, 2013.
Biologically Active Substances of Plant Origin, Russian Academy of Sciences, 2001, ., ., RU.
Castor Oil, Wikipedia (website), ., 1-4, ., US.
A. Perez-Vasquez et al., Antimicrobial activity and chemical composition of the essential oil of Hofmeisteria schaffneri, Journal of Pharmacy and Pharmacology, Aug. 5, 2010, 579-586, vol. 63.
Abdeslam Jaafari, Hassan Ait Mouse, El Mostapha Rakib et al, Chemical composition and antitumor activity of different wild varieties of Moroccan thyme, Brazilian Journal of Pharmacognosy, Aug. 27, 2007, 477-491, 17(4).
Achi, Composition and Antibacterial Activities of Tetrapleura tetraptera Taub, Research Journal of Microbiology, 2006, 416-422, vol. 1 No. 5, US.
Banayeva, A Study of the Chemical Composition of the Essential Oil of Representatives, Vegetable feed chemistry, 1999, 41-48, 3, RU.
Banayeva, The study of the chemical composition of an essential oil, Vegetable feed chemistry, 1999, 41-48, No. 3, RU.
Botelho et al., Antimicrobial activity of the essential oil from Lippia sidoides, carvacrol and thymol against oral pathogens, Brazilian Journal of Medical and Biological Research, 2007, 349-356, 40.
Budavari (Editor), An Encyclopedia of Chemicals, Drugs, and Biologicals, The Merck Index, 1996, 1568, 12th Edition, Merck Research Laboratories, Whitehouse Station, US.
Burt et al, Essential oils: their antibacterial properties and potential application in foods—a review, Int J of Food Microbiology, 2004, 223-253, 94.
CEN Members, Chemical disinfectants and antiseptics—Quantitative suspension test for the evaluation of bactericidal activity of chemical . . . , European Standard, Jan. 1, 1997, 1-18, EN 1276.
Coco et al., Candida biofilms in denture stomatitis: novel detection and treatment methods, The Pan European Federation of the Internatnional Association for Dental Research, Sep. 11, 2008.
Davies A., Action of Biguanides, Phenols and detergents on Escherichia coli and its spheroplasts, Action of Biguanides, 1969, 233-243, 32.
Dimitrijevic, et al., A study of the synergistic antilisterial effects of a sub-lethal dose of lactic acid and essential oils, Food Chemistry, Jan. 1, 2007, 774-782, 104, Elsevier, US.
Evandro Leite De Souza, Interference of heating on the antimicrobial activity and chemical composition of Origanum vulgare L. (Lamiaceae) essential oil, Interference of heating on the antimicrobial activity and chemical composition of Origanum vulgare L. (Lamiaceae) essential oil, Apr. 1, 2008, 1-7, vol. 28, No. 2.
Figueredo et al, Studies of mediterranean oregano populations. VIII—Chemical composition of essential oils of oreganos of various origins, Flavour and Fragrance Journal, May 9, 2005, 134-139, 21.
Friedman, et al., Antibacterial Activities of Naturally Occurring Compounds Against Antibiotic-Resistant Bacilllus cereus, Journal of Food Protection, Mar. 12, 2004, 1774-1778, 67, No. 8, Journal of Food Protection, US.
Gablin, Balsamic fragrances Lemon thyme, Handmade Soaps, Jul. 18, 2007, 84, ., RU.
Hong S, Antimicrobial Activity of Tyramine Derivatives, Antimicrobial Activity of Tyramine Derivatives, Oct. 29, 2000, NA, NA.
IPRP in PCTEP2012074399, Jul. 10, 2014, pp. 1-20, WO.
IPRP2 in PCTEP2012074409, Jul. 10, 2014.
IPRP2 in PCTEP2012074416, Jul. 10, 2014.
Jalali-Heravi et al, Analysis of Iranian rosemary essential oil: application of gas chromatography-mass spectrometry combined with chemometrics, Journal of Chromatography A, Mar. 21, 2011, 2569-2576, 1218.
Karabit et al, Studies on the evaluation of preservative efficacy III. The determination of antimicrobial characteristics of benzalkonium chloride, Int J of Pharmaceutics, 1988, 141-147, 46.
Kirchner et al, Chemical composition and antimicrobial activity of Hedyosmum brasiliense Miq., Chloranthaceae, essential oil, Brazilian Journal of Pharmacognosy, Jan. 11, 2010, 692-699, 20(5).
Kisgyorgy et al, Essential oil of the more important indigenous Thymus species occurring in the composition of Serpylli herba, Farmakognoziai Tansz., Jan. 1, 1983, 124-130, 29.
Kubo et al, Antimicrobial activity of anethole and related compounds from aniseed, Journal of the Science of Food and Agriculture, 2008, 242-247, 88.
Leung A Y; Foster, Encyclopedia of common and natural ingredients used in food, drugs and cosmetics, Cinnamon (and Cassia), Jan. 1, 1996, pp. 167-170,260-264,393-397,405-408,492-494,510-511, ISBN: 978-0-471-50826-7.
M. Sebesan, Analysis of the I,II Essential Oils from Thyme (Thymus vulgaris L) and from Peppermint (Mentha piperita L), Analysis of the I,II Essential Oils from Thyme and from Peppermint, Dec. 31, 2008, 212-214, Retrieved from the Internet.
Mah J H, *Paenibacillus tyraminigenes* sp. nov. isolated from Myeolchi-jeotgal. a traditional Korean salted and fermented anchovy, *Paenibacillus tyraminigenes* sp. nov. isolated from Myeolchi-jeotgal., Oct. 31, 2008, pp. 209-214, vol. 127. No. 3.
Majnooni et al, Chemical composition, cytotoxicity and antioxidant activities of the essential oil from the leaves of citrus aurantium L, African Journal of Biotechnology, May 1, 2012, 498-503, 11(2).
Miladinovie et al, Investigation of the chemical composition—antibacterial activity relationship of essential oils by chemometric methods, Anal Bioanal Chem, Mar. 3, 2012, 1007-1018, 403.
Naigre Ruth, Comparison of antimicrobial properties of monoterpenes and their carbonylated products, Comparison of antimicrobial properties of monoterpenes and their carbonylated products, 1996, 275-277, vol. 62, No. 3.
Oyedemi et al., The proposed mechanism of bactericidal action of eugenol, a-terpineol and y-terpinene against listeria monocytogened, streptococcus pyogenes, proteurs vulgaris and *Escherichia coli*, African Journal of Biotechnology, Apr. 6, 2009, 1280-1286, 8(7).
Rossi et al, Chemical fingerprinting and bioactivity of Amazonian Ecuador croton lechleri Mull. Arg (Euphorbiaceae) stem bark essential oil: A new functional food ingredient?, Food Chemistry, Jun. 1, 2011, 837-848, 126.
Sagoo SK, Chitosan potentiates thE antimicrobial action of sodium benzoate on spoilage yeasts, Chitosan and Benzoate, Jan. 3, 2008, 168-172, 34—No. 3.
Sato et al, Antimicrobial effect of trans-cinnamaldehyde, (−)-perillaldehyde, (−)-citronellal, citral, eugenol and carvacrol on airborne microbes using an airwasher, Biol Pharm bull, 2006, 2292-2294, 29(11).
Sawamura et al, Characteristic odor components of citrus reticulata blance (Ponkan) cold-pressed oil, Biosci. Biotechnol. Biochem., Apr. 16, 2004, 1690-1697, 68(8).

(56) References Cited

OTHER PUBLICATIONS

Shixiang, Anticorrosive functions of convention flavors and fragrances, Toothpaste Industry, 2000, 23-27, 2, CN.
Singh et al., Antioxidant and antimicrobial activities of essential oil and various oleoresins of Elettaria cardamomum (seeds and pods), Journal of the Science of Food and Agriculture, Mar. 6, 2007, 280-289, 88.
Tian et al, Chemical composition and antifungal activity of essential oil from cicuta virosa L. var. latisecta celak, International Journal of Food Microbiology, Jan. 1, 2011, 464-470, 145.
Tippayatum et al, Antibacterial activities of thymol, eugenol and nisin against some food spoilage bacteria, Nat Science, 2007, 319-323, 41.
Umback et al., Georg Thieme Verlag, Kosmetik, 1995, 360-369, ., DE.
Van Der Wolf, Disinfection of vegetable seed by treatment with essential oils, Seed Science and Technology, 2008, 76-88, 36, US.
Wang, Synergistric Antimicrobial Activities of Natural Oils with Chitosan Films, Journal of Agricultural and Food Chemistry, Oct. 29, 2011, 12411-12419, vol. 59 No. 23, ACS Publications, US.
Younhee Byun et al., Analysis of Composition and Activity of Essential Oil from Chrysanthemum zawadskii var. latilobum and C. indicum against Antibiotic-Resistant Pathobenic Bacteria, Natural Product Sciences, Jun. 16, 2008, 138-142, vol. 14-No. 2.
Yu et al., Chemical composition and antimicrobial activity of the essential oil of *Scutellaria barbata*, Phytochemistry 65 (2004), Sep. 5, 2003, 881-884, 65.
Zhigzhitzhapova, Chemical composition of an essential oil of Baikal thyme, Vegetable feed chemistry, 2008, 73-76, No. 1, RU.
Zhigzhitzhapova, The Chemical Composition of the Essential Oil of Baikal Thyme, Vegetable fee chemistry, 2008, 73-76, 1, RU.
Zrira et al, Chemical composition of the essential oil of nine eucalyptus species growing in Morocco, Flavour and fragrance journal, Apr. 2, 2004, 172-175, 19.
Bechtold et al, Extraction of natural dyes for textile dyeing from coloured plant wastes relased from the food and beverage industry, Journal of the Science of Food and Agriculture 2006 vol. 86 p. 233-242 Abstract, Nov. 14, 2005, pp. 233-242, 86.
Bechtold et al, Extraction of natural dyes for textile dyeing from coloured plant wastes released from the food and beverage industry, Journal of the science of food and agriculture 2006 vol. 86 p. 233-242, Nov. 14, 2005, pp. 233-242, 86.
Christoph et al., Glycerol, Ullmann's Encyclopedia of Industrial Chemistry, 2012, pp. 67-82. NB: only relevant pp. 67-69 and 79., vol. 17, Wiley-VCH Verlag GmbH & Co. KGaA, Weinheim.
Darwish et al., Effects of Hydrotropic Agents on the Solubility, Precipitation, and Protein Binding of Etoposide, Journal of Pharmaceutical Sciences, 1989, pp. 577-581, vol. 78 No. 7.
IPRP in PCTEP2012073193, Mar. 28, 2014.
IPRP2 in PCTEP2011070093, Mar. 22, 2013.
IPRP2 in PCTEP2012073005, Apr. 9, 2014.
Joulain et al., The Absolute From flowers of Jasminum auriculatum Vahl from India, Flavour and Fragrance Journal, 1995, pp. 193-197, vol. 1.
Notice of Opposition (Biersdorf) in EP2348838 (09783843), Feb. 6, 2014.
Notice of Opposition (Henkel) in EP2348838 (09783843), Feb. 7, 2014.
Peleg et al., Bitterness and astringency of flavan-3-ol monomers, dimers and trimers, Journal of the Science of Food and Agriculture, Jan. 1, 1999, 1123-1128, 79.
Search Report in EP12152564, Aug. 27, 2012.
Search Report in PCTEP2010062982, Dec. 28, 2010.
Search Report in PCTEP2012073005, Mar. 25, 2013.
Search Report in PCTEP2012073193, Mar. 18, 2014.
Takeshi Deyama Etc., Studies on the Components of Essential Oil of Clove, Yakugaku Zasshi (Abstract), 1971, pp. 1383-1386, 91(12).
Walter Feldheim, Investigation of the presence and significance of theanine in the tea plant, Investigation of the presence and significance of theanine in the tea plant, Jan. 1, 1986, 537-534, 37-6.
Written Opinion in EP12152561, Aug. 27, 2012.
Written Opinion in EP12152564, Aug. 12, 2012.
Written Opinion in PCTEP2010062982, Dec. 28, 2010.
Written Opinion in PCTEP2012073005, Jan. 23, 2014.
Written Opinion in PCTEP2012073193, Mar. 18, 2014.
Written Opinion1 in PCTEP2012073193, Jan. 15, 2014.
IPRP2 in PCTEP2011070314, Apr. 5, 2013, WO.
IPRP2 in PCTEP2012074402, Aug. 21, 2014.
IPRP2 in PCTEP2013062187, Aug. 22, 2014.
Search Report & Written Opinion in EP15198664, Feb. 9, 2016.
Search Report in EP09175200, Feb. 8, 2010, EP.
Search Report in EP11151946, Jul. 7, 2011, EP.
Search Report in EP12150935, May 15, 2012.
Search Report in EP12150937, Apr. 25, 2012, EP.
Search Report in EP12151770, Aug. 2, 2012, EP.
Search Report in EP12168864, Aug. 13, 2012.
Search Report in EP12183546, Jan. 16, 2013.
Search report in PCTEP2011070314, Feb. 6, 2012, WO.
Search Report in PCTEP2013062187, Aug. 18, 2013.
Wei Wende (ED.), Cyclopedia of Organic Chemical Materials, Cyclopedia of Organic Chemical Materials, 1999, p. 935 (and Cover page)—in Chinese only, no Engl abstract or translation available, vol. II (Second Edition).
Written Opinion in EP12168864, Aug. 13, 2012.
Written Opinion in EP09175200, Feb. 8, 2010, EP.
Written Opinion in EP10169778, May 12, 2011.
Written Opinion in EP11151946, Jul. 11, 2011, EP.
Written Opinion in EP12150935, May 15, 2012.
Written Opinion in EP12150937, May 4, 2012, EP.
Written Opinion in EP12151770, Aug. 2, 2012, EP.
Written Opinion in EP12183546, Jan. 16, 2013.
Written Opinion in EP12794989, Jun. 1, 2015, EP.
Written Opinion in EP12797891, Jun. 1, 2015, EP.
Written Opinion in EP12798329, Jul. 24, 2015, EP.
Written Opinion in EP12798699, Dec. 11, 2015.
Written Opinion in PCTEP2011070314, Feb. 6, 2012, WO.
Written Opinion in PCTEP2013062187, Aug. 18, 2013.

\* cited by examiner

ORAL CARE COMPOSITION

TECHNICAL FIELD

The present invention relates to an oral care composition and a method of disinfecting the oral cavity.

BACKGROUND AND PRIOR ART

Oral hygiene is one of the most important aspects of personal care among consumers. Consumers all over the world use different types of products for oral care. People routinely brush their teeth with a toothbrush and a dentifrice which may be a toothpaste or a toothpowder at least two times a day. Use of such brushing ensures maintaining good oral hygiene by minimising oral bacteria that accumulate in the mouth over the course of sleeping in the night or during the course of the day when people eat their food and consume beverages. Brushing, thus minimises problems like cavities, tartar, gingivitis, caries, and bad breath, also known as halitosis.

In spite of brushing teeth twice a day, many people suffer from various forms of one or more of the above named diseases and this is believed to be caused by bacteria acting in the oral mucosa over the about twelve hour period between brushing. During such times, people resort to rinsing/gargling their mouth with an antiseptic mouthwash. Most antiseptic mouthwashes contain a substantial amount of alcohol (e.g. ethyl alcohol or isopropyl alcohol) for killing oral bacteria.

In solving the above oral care problems, the approach so far has been to use synthetic materials (e.g. Triclosan) which are believed by many consumers to be harsh on them. Consumers, more and more, especially of late, prefer using products that contain natural materials. Further, in many countries, culturally or otherwise, people are reluctant to using alcohol in their mouthwashes.

The present inventors have been working on solving these problems and have come up with an oral care composition which includes natural materials that are found to interact synergistically with certain metal salts in killing *S. mutans*, a bacterium responsible for tooth decay.

Essential oils actives have been cited in prior publications in oral care.

JP2196718 (Kowa, 1989) discloses a liquid for external use having increased solubility and stability, containing 0.1 to 5% indomethacin and a 0.3 to 10% dissolution auxiliary as essential components, the dissolution auxiliary selected from limonene, pinene, camphene, cymene, citronellol, geraniol, nerol, linalool, terpineol, rhodinol, borneol, isoborneol, menthone, camphor, thymol, safrole, isosafrole, eugenol and isoeugenol.

WO 00/00166 (Warner Lambert) discloses an oral composition that includes thymol, a zinc salt and a sweetener is disclosed. The oral composition has antitartar, antiplaque, antigingivitis efficacy, long lasting breath freshening and high consumer acceptability in spite of the presence of two ingredients, thymol and a zinc salt, that are known to taste bad.

None of the publications, to date, teach that a mixture of antimicrobial essential oil actives thymol and terpineol when used along with a specific metal salt provides for fast acting anti-microbial action, in a synergistic way. The present inventive combination provides vastly improved and synergistic anti-bacterial efficacy as compared to a combination of zinc salt and thymol as disclosed in WO 00/00166.

It is an object of the present invention to overcome or ameliorate at least one of the disadvantages of the prior art, or to provide a useful alternative.

Another object of the present invention is to provide for an antimicrobial composition that has relatively fast antimicrobial action in killing bacteria in the oral cavity.

SUMMARY OF THE INVENTION

The first aspect of the present invention provides for an oral care composition comprising
(i) 0.05 to 10% of an antimicrobial essential oil comprising thymol and terpineol, such that the composition comprises
0.03 to 0.4% by weight thymol, and
0.06 to 0.6% by weight terpineol;
(ii) 0.1 to 5% of a zinc salt; and
(iii) an orally acceptable base;
wherein the zinc salt is zinc halide, zinc sulphate, zinc acetate or zinc phosphate;
and wherein the combination of the thymol, the terpineol and the zinc salt provides synergistic anti-bacterial efficacy against *Streptococcus mutans*.

The second aspect of the present invention provides for a method of disinfecting the oral cavity comprising the steps of
(i) applying a composition of the first aspect onto the oral cavity; and
(ii) cleaning the cavity to be substantially free of said composition.

The third aspect of the present invention provides for use of a composition comprising
(i) 0.05 to 10% of an antimicrobial essential oil comprising thymol and terpineol, such that the composition comprises
0.03 to 0.4% by weight thymol, and
0.06 to 6% by weight terpineol; and
(ii) 0.1 to 5% of a zinc salt;
for disinfecting the oral cavity;
wherein the zinc salt is zinc halide, zinc sulphate, zinc acetate or zinc phosphate;
and wherein the combination of the thymol, the terpineol, and the zinc salt provides synergistic anti-bacterial efficacy against *Streptococcus mutans*.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Unless specified otherwise, numerical tinges expressed in the format "from x to y" are understood to include x and y. When for a specific feature multiple preferred ranges are described in the format "from x to y", it is understood that all ranges combining the different endpoints are also contemplated.

The compositions of the present invention are preferred for non-therapeutic use, and more particularly preferred for use in disinfecting surfaces of the oral cavity.

The first aspect of the present invention provides for an oral care composition comprising 0.05 to 10% of an antimicrobial essential oil comprising thymol and terpineol as described below, 0.1 to 5% of a zinc salt; and an orally acceptable base.

The composition preferably comprises 0.1 to 5% of essential oil. The essential oil comprises thymol and terpineol and preferably also comprises components selected from eugenol, horned, limonene, iso-borneol, eucalyptol, camphor or a mixture thereof. More preferably, the essential oil also comprises eugenol.

Eugenol

Eugenol is an allyl chain-substituted guaiacol. It is generally extracted from certain spices like clove or cinnamon. Eugenol has been used as a perfumery component, in preparing flavors, as an antiseptic or as a local anesthetic. The composition of the invention preferably comprises 0.005 to 5%, preferably 0.02 to 1%, more preferably 0.03 to 0.4%, by weight eugenol.

Eugenol has the structure:

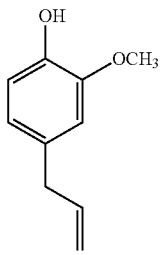

Thymol

The structure of thymol is given below:

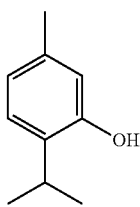

The composition of the invention comprises 0.03 to 0.4%, by weight thymol. Thymol may be added to the composition in purified form. Alternatively, thyme oil or thyme extract comprising thymol may be added to the composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*.

Terpineol

The structure of a terpineol compound is given below:

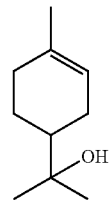

The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form. Alternatively pine oil comprising terpineol may be added to the antimicrobial composition while ensuring that terpineol is present in the desired concentration in the composition of the present invention. The composition comprises 0.06 to 0.6% by weight terpineol.

The composition may preferably comprise a combination of thymol and terpineol in any of the preferred concentrations as specified above for thymol and terpineol, respectively.

For instance, the composition may preferably comprise a mixture of 0.03 to 0.6% thymol and 0.06 to 1.5% terpineol by weight of the composition. The composition of the present invention most preferably comprises a mixture of 0.03 to 0.4% eugenol, 0.03 to 0.6% thymol, and 0.06 to 1.5% terpineol by weight of the composition.

Zinc Salt

Preferred zinc salts are zinc halide (preferably chloride or bromide), zinc sulphate, zinc acetate, or zinc phosphate. The composition comprises 0.1 to 5% zinc salt.

Orally Acceptable Base

The antimicrobial composition comprises an orally acceptable base. The orally acceptable base depends on the format in which the oral care composition is delivered. Most suitable formats are an antiseptic mouthwash, a toothpaste or a toothpowder.

Mouthwash

When the composition is formulated as an antiseptic mouthwash, the orally acceptable base is water. The desired antibacterial efficacy in the mouthwash of the present invention can be obtained without the use of low molecular weight (C1 to C3) alcohols e.g. ethanol or isopropyl alcohol, i.e the composition is preferably substantially free of low molecular weight alcohol. By the term substantially free of low molecular weight alcohols is meant that the alcohol may be present in an amount which does not significantly affect the microbial kill. Preferably, C1 to C3 alcohols are present in leas than 2%, more preferably less than 1% and most preferably absent from the composition of the invention.

Thus, the invention, provides an antimicrobial mouthwash composition according to the first aspect of the invention (i.e. comprising thymol, terpineol and a zinc salt) also comprising 80 to 99.9% water. The antimicrobial mouthwash composition of the invention preferably comprises 0.05 to 10%, more preferably 0.05 to 8%, most preferably 0.5 to 5% of a surfactant by weight of the composition. The surfactant is preferably of the cationic, anionic, or zwitterionic class, most preferably of the cationic class. When anionic surfactant is present it is preferably chosen from alkali or alkaline earth metal salts of alkyl sulphonic acid, fatty acid, or alkyl ether sulphate. When zwitterionic surfactant is present it is preferably chosen from betaines, sulphobetains, hydroxyl sulphobetains, or amino carboxylates When a cationic surfactant is present it is benzalkonium chloride, alkyl pyridinium chloride or quaternary ammonium gemini surfactants.

The antimicrobial mouthwash composition of the invention is used for disinfecting the oral cavity either by using the composition with no dilution or after diluting the composition with water. The preferred weight ratio of composition to water for the dilution step is in the range of 1:1 to 1:200, more preferably 1:5 to 1:50, further more preferably 1:15 to 1:30 and ideally about 1:20.

Toothpaste

The composition of the invention may be delivered in a toothpaste format. When the composition is a toothpaste, the orally acceptable base is an abrasive which may be calcium carbonate or abrasive silica. When calcium carbonate is the abrasive, the toothpaste is in the opaque paste format. When abrasive silica is used, the toothpaste is usually delivered in the transparent gel format. Toothpastes also preferably comprise a surfactant in 2 to 15% by weight of the composition. Preferred surfactants are anionic or amphoteric in nature. Anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear C10~C18 chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Opaque Toothpaste

When calcium carbonate is the abrasive, it is usually present in 15 to 70%, more preferably in 30 to 60% by weight of the composition.

Calcium carbonate (also known as chalk) is available in many forms and some of these forms are used in oral care compositions. Two commonly used forms are FGNC (fine ground natural chalk) and PCC (precipitated calcium carbonate). Of the total chalk content in the oral care composition, FGNC, is generally present in 35 to 100% preferably from 75 to 100% and especially from 95 to 100%, the balance being PCC. Typically, the FGNC will comprise from 30 to 65%, preferably from 35 to 55% and most preferably from 40 to 55% by weight of the composition.

FGNC generally comprises particles of weight-based median particle size ranging from 1 to 15 μm, preferably from 2 to 10 μm and especially from 4 to 7 μm.

The composition may also include other known "non-chalk" abrasives to improve the abrasive action. Such abrasives include dicalcium phosphate dihydrate (DCPD) and silica.

In addition to calcium carbonate, one can also include abrasive silica in opaque toothpastes for enhanced abrasive action. The abrasive silica may be included in 4 to 15%, preferably 6 to 12%, and further more preferably 7 to 10%. Alternatively perlite may be included in 0.0.1 to 2%, preferably in 0.1 to 0.8%, further more preferably 0.3 to 0.7% by weight of the composition.

Water in these toothpastes is generally included in 15 to 40%, preferably 20 to 30% by weight of the composition.

Preferred compositions include a humectant, e.g. xylitol, glycerol or sorbitol. Glycerol and sorbitol are particularly preferred. Preferably, the compositions include 0.1 to 20 wt % humectant. More preferred compositions include 1 to 15 wt % humectants while further preferred compositions include 5 to 13 wt % humectants.

The compositions preferably also include an alkali-metal bicarbonate salt. Preferably the alkali-metal bicarbonate salt is a sodium salt, from 1 to 30 wt %, more preferably from 2 to 20 wt % and especially from 3 to 8 wt %.

Gel Toothpaste

Preferred compositions to prepare gel toothpaste comprise an abrasive silica. They preferably have a low refractive index in the range of 1.41-1.47, preferably 1.435-1.445, preferably having a weight mean particle size of between 5 and 15 micrometer, a BET (nitrogen) surface area of between 10 and 100 $m^2/g$ and an oil absorption of about 70-150 $cm^3/100$ g. Typical examples of suitable low refractive index abrasive silicas are Tixosil 63 and 73 ex Rhone Poulenc; Sident 10 ex Degussa; Zeodent 113 ex Zeofinn; Zeodent 124 ex Huber, Sorbosil AC series supplied by Crosfield, for example Sorbosil ACI1, Sorbosil AC39 and Sorbosil AC35, particularly Sorbosil AC 77 ex Crosfield Chemicals. The amount of these silicas in the composition generally ranges from 2-60% by weight, usually 2-20% by weight and more preferably 5 to 12 wt %.

Thickening silica may also be incorporated in gel toothpastes. They are usually incorporated in 4 to 12%, preferably 5 to 10% by weight of the composition. Preferred grades are medium thickening silica such as MFIL (ex. Madhu Silica India), TC15 (from PQ Corp UK), and Zeodent 165 Ex. Huber, or Tixosil 43 from Rhodia.

Water in these toothpastes is generally included in 8 to 14%, preferably 8 to 10% by weight of the composition. These amounts of water are exclusive of water which are incorporated in the composition from aqueous solutions of other ingredients e.g. sorbitol.

The compositions for any type of toothpaste (opaque or gel type) may also include an anti-caries agent, binders, thickeners, flavours, stabilizing agents, polymers, vitamins, buffers and anti-calculus agents.

Thus, according to a preferred embodiment of the invention there is provided a toothpaste composition according to the first aspect of the invention, also comprising 2 to 70% of an abrasive selective from calcium carbonate or silica; and 8 to 40% water.

Toothpowder

Toothpowders usually have very high percentage of abrasives. Chalk (FGNC) is the most preferred one but PCC can also be used. Usual percentages of such abrasives are from 90 to 99.9%, preferably 90 to 95% by weight of the composition. Desired amount of foam is provided by including an anionic surfactant e.g. Sodium Lauryl Sulphate in the toothpowder composition. The surfactant may be incorporated from 2 to 3% in the composition. Other ingredients like silica or Sodium monofluoro phosphate may be included at up to about 1 weight % of the composition.

Sweeteners such as xylitol, sorbitol, glycerol or sachharin may be included. Flavors such as spearmint or peppermint may be included at up to 1 weight % of the toothpowder composition.

The present invention therefore also provides a toothpowder composition according to the first aspect of the invention, comprising 90 to 99.9% of an abrasive selected from calcium carbonate or silica.

Thus, in the composition of the present invention the orally acceptable base is preferably selected from water, silica, or calcium carbonate.

An aspect of the present invention provides for a method of disinfecting the oral cavity comprising the steps of (i) applying a composition of the invention on to the oral cavity; and (ii) cleaning the cavity, to be substantially free of said composition. By cleaning is meant that the composition is substantially removed from the oral cavity. The composition, when in liquid form (e.g. a mouthwash) is simply spat out. When the composition is in powder, paste or gel form the composition may be rinsed off from the oral cavity using suitable amount of water. When the composition is a toothpaste, it is generally brushed on to the teeth or gums in the oral cavity before the step of rinsing. Rinsing is usually done by taking water and washing or gargling the mouth with this water.

Yet another aspect of the present invention provides for use of a composition comprising
  (i) 0.05 to 10% of an antimicrobial essential oil comprising thymol and terpineol, such that the composition comprises
    0.03 to 0.4% by weight thymol, and
    0.06 to 0.6% by weight terpineol; and
  (ii) 0.1 to 5% a zinc salt;
for disinfecting the oral cavity;
wherein the zinc salt is zinc halide, zinc sulphate, zinc acetate or zinc phosphate;
and wherein the combination of the thymol, the terpineol, and the zinc salt provides synergistic anti-bacterial efficacy against *Streptococcus mutans*.

The invention preferably provides for non-therapeutic benefits.

EXAMPLES

The invention will now be demonstrated with examples. The examples are for purpose of illustration only and do not limit the scope of claims in any manner.

Examples 1 to 5

Synergistic Interaction of the Ingredients of the Composition of the Invention

*Streptococcus mutans* (*S. mutans*) is a Gram-positive, facultatively anaerobic bacterium commonly found in the human oral cavity. *S. mutans* is the leading cause of dental caries (tooth decay) worldwide and is considered to be the most cariogenic of all of the oral streptococci. *S. mutans*, sticks to the surface of teeth and subsists on a diverse group of carbohydrates. While metabolising sugar and other energy sources, the microbe produces acid that causes cavities in teeth.

Various Compositions as Shown in Table-1 were Prepared.

The compositions listed in Table-1 were used to test the efficacy as an antibacterial composition against *S. mutans* in a 15 second contact test in suspension, using the following procedure.

The test bacteria *S. mutans* was grown overnight at 37° C. in BHI broth under 5% $CO_2$ ($CO_2$ incubator). Then the culture was processed and the cell density was adjusted at 620 nm to get the final count of $10^8$ cfu/ml (0.3 OD). 9 ml of the compositions was taken in a sample container and 1 ml of processed culture was added to it. After a 15 second contact time 1 ml of the above mixture was immediately neutralized in D/E broth. This was serially diluted in D/E broth and plated in BHI agar in duplicates. In case of the control, 1 ml of test culture was added to 9 ml of saline and was serially diluted and plated on BHI agar. After solidification, the plates were incubated at 37° C. under 5% $CO_2$ for 48 hrs. The residual colonies were counted after 48 hours and the log reduction of bacteria with respect to the control sample was calculated. The data are compiled in Table 1.

TABLE 1

| Ingredient | Example 1 wt % | Example 2 wt % | Example 3 wt % | Example 4 wt % | Example 5 wt % |
|---|---|---|---|---|---|
| Zinc sulphate | 0.2 | — | 0.2 | — | 0.2 |
| Thymol | — | 0.125 | 0.125 | — | 0.125 |
| Terpineol | — | — | — | 0.25 | 0.25 |
| Water | To 100 | To 100 | To 100 | To 100 | To 100 |
| Log reduction | 0 | 0.1 | 0.4 | 0 | 7.1 |

The data in Table 1 indicate that the composition as per the invention (Example-5) provides for synergistic anti-bacterial efficacy as compared to using a combination of thymol and zinc salt (Example 3 as disclosed in WO 00/000166) and when using terpineol alone (Example-4).

Examples 6-8

Efficacy of Various Compositions Against *S. mutans* in a One Minute Contact Test in Suspension Various compositions as shown in Table-2 were prepared.

The compositions listed in Table-2 were used to test the efficacy as an antibacterial composition against *S. mutans* in a one minute contact test in suspension, using the following procedure.

Culture *S. mutans* was taken in a BHI broth [and was allowed to grow in $CO_2$ incubator (15% $CO_2$) at 37° C. for 15 hours]. The *S. mutans* culture was adjusted to a optical density to 0.3 (~$10^8$ cfu/ml) at 620 nm. 9 ml of the desired composition was taken and added to 1 ml of culture and mixed. After a one minute contact time with the culture, they were neutralized in D/E broth and after serial dilution they were plated in BHI Agar. The plates were incubated in $CO_2$ incubator. The residual colonies were counted after 48 hours of incubation. The efficacy compared to a control sample was measured and the data is compiled in Table-2.

The amount of log reduction of the bacteria was measured and the data is summarized in Table 2.

TABLE 2

| Ingredient | Example 6 Wt % | Example 7 Wt % | Example 8 Wt % |
|---|---|---|---|
| Terpineol | 0.125 | — | 0.125 |
| Thymol | 0.250 | — | 0.250 |
| Eugenol | 0.025 | — | 0.025 |
| Zinc Sulphate | — | 0.120 | 0.120 |
| Water | To 100 | To 100 | To 100 |
| Log reduction of bacteria | 1.0 | 0.2 | 7.3 |

The data in Table 2 indicate that the antibacterial efficacy of a composition of the invention (Example 8) demonstrates synergistic antibacterial activity with respect to essential oil active combination of thymol, terpineol and eugenol (Example 6) and zinc salt composition alone (Example 7).

The invention claimed is:
1. An oral care composition comprising
  (i) 0.05 to 10% of an antimicrobial essential oil comprising thymol and terpineol, whereby the composition comprises

0.03 to 0.4% by weight thymol, and
0.06 to 0.6% by weight terpineol;
(ii) 0.1 to 5% of a zinc salt; and
(iii) an orally acceptable base;
wherein the zinc salt is zinc halide, zinc sulphate, zinc acetate or zinc phosphate;
and wherein the combination of the thymol, the terpineol and the zinc salt provides synergistic anti-bacterial efficacy against *Streptococcus mutans*.

2. A composition as claimed in claim 1 comprising 0.1 to 5% antimicrobial essential oil.

3. A composition as claimed in claim 1 wherein said antimicrobial essential oil also comprises eugenol, such that the composition comprises 0.005 to 5% of eugenol.

4. A composition as claimed in claim 3 comprising 0.03 to 0.4% eugenol by weight of the composition.

5. A composition as claimed in claim 1 wherein said orally acceptable base comprises water, silica, or calcium carbonate.

6. A composition as claimed in claim 1 comprising 2 to 15% surfactant.

7. An antimicrobial mouthwash comprising the composition according to claim 1 and also comprising 80 to 99.9% water.

8. A toothpaste comprising the composition according to claim 1 and also comprising
(i) 2 to 70% of an abrasive selective from calcium carbonate or silica; and
(ii) 8 to 40% water.

9. A toothpowder comprising the composition according to claim 1 and also comprising 90 to 99.9% of an abrasive selected from calcium carbonate or silica.

10. A method of disinfecting the oral cavity comprising the steps of
(i) applying a composition as claimed in claim 1 onto the oral cavity; and
(ii) cleaning the cavity to be substantially free of said composition.

11. A method as claimed in claim 10 wherein said composition is brushed on to the teeth or gums in the oral cavity before said step of rinsing.

* * * * *